United States Patent
Boucher et al.

(10) Patent No.: US 9,986,749 B2
(45) Date of Patent: Jun. 5, 2018

(54) METHOD OF PROTECTING ACTIVE INGREDIENTS FROM DEGRADATION DURING PELLETING

(71) Applicant: Purina Animal Nutrition LLC, Shoreview, MN (US)

(72) Inventors: Sarah E. Boucher, Des Moines, IA (US); Jill Davidson, Washington, MO (US); Bill L. Miller, Labadie, MO (US)

(73) Assignee: PURINA ANIMAL NUTRITION LLC, Shoreview, MN (US)

(*) Notice: Subject to any disclaimer, the term of this patent is extended or adjusted under 35 U.S.C. 154(b) by 406 days.

(21) Appl. No.: 13/957,877

(22) Filed: Aug. 2, 2013

(65) Prior Publication Data

US 2014/0037709 A1 Feb. 6, 2014

Related U.S. Application Data

(60) Provisional application No. 61/678,910, filed on Aug. 2, 2012.

(51) Int. Cl.

| | |
|---|---|
| *A61K 9/50* | (2006.01) |
| *A23K 1/00* | (2006.01) |
| *A23K 40/10* | (2016.01) |
| *A23K 40/30* | (2016.01) |
| *A23K 40/35* | (2016.01) |
| *A23K 20/105* | (2016.01) |
| *A23K 20/142* | (2016.01) |
| *A23K 50/10* | (2016.01) |

(52) U.S. Cl.
CPC ............ *A23K 1/005* (2013.01); *A23K 20/105* (2016.05); *A23K 20/142* (2016.05); *A23K 40/10* (2016.05); *A23K 40/30* (2016.05); *A23K 40/35* (2016.05); *A23K 50/10* (2016.05); *A61K 9/5015* (2013.01)

(58) Field of Classification Search
CPC ........ A23K 1/002; A23K 1/004; A23K 1/005; A23K 1/1609; A23K 1/1634; A23K 1/1813; A61K 9/5015
See application file for complete search history.

(56) References Cited

U.S. PATENT DOCUMENTS

| | | | | |
|---|---|---|---|---|
| 5,871,773 | A * | 2/1999 | Rode | A23K 40/35 424/438 |
| 6,306,427 | B1 | 10/2001 | Annonier et al. | |
| 2005/0019413 | A1 * | 1/2005 | Cavassini et al. | 424/489 |
| 2007/0172540 | A1 * | 7/2007 | Neece | A23K 40/10 426/2 |
| 2011/0250286 | A1 * | 10/2011 | Marcello | A61K 9/0068 424/498 |

\* cited by examiner

*Primary Examiner* — Michael B. Pallay
(74) *Attorney, Agent, or Firm* — Dorsey & Whitney LLP

(57) ABSTRACT

A system for the protection against degradation during pelleting of one or more physiologically or pharmacologically active substances, comprising compositions in the form of micro particles or granules, particularly for use in the zootechnical and/or veterinary field. The micro particles include a core which contains one or more substances having a pharmacological action, food supplements or diagnostic media, said one or more substances being characterized by the presence, within their chemical structure, of a basic functional group, specifically including an amine functional group. The core comprises also one or more carboxylic acids and/or their salts and eventually one or more excipients. Said core is coated by an outer layer of fats or waxes, and preferably by a mixture of glyceride of fatty acids.

19 Claims, No Drawings

METHOD OF PROTECTING ACTIVE INGREDIENTS FROM DEGRADATION DURING PELLETING

This application claims priority to U.S. Patent Application Ser. No. 61/678,910, filed Aug. 2, 2012.

BACKGROUND OF THE INVENTION

The present invention relates generally to compositions in the form of micro particles and, more specifically, to micro particles intended for use in the zootechnical field and/or in the veterinary field.

The oral administration of active substances in the zootechnical field is a problem which is not easy to solve, in particular as regards the possibility to ensure intestinal absorption of adequate doses of said substances, avoiding their massive degradation during passage through the digestive tract of the animal, especially in the case of ruminants. Another problem is the degradation of the active substances during pelleting in the creation of feed products where it is not unusual to see a 50% loss in bioavailability of the active ingredients.

SUMMARY OF THE INVENTION

The invention enables the controlled release of active ingredients in the gastrointestinal tract of animals, particularly ruminants, and protects the active ingredients during the processing of the ingredients by pelleting. The technology and formulations described are capable of controlling the release of one or more substances which have a pharmacological action or play a role as feed supplements. In such compositions, the substance or substances carried by the micro particles are protected against the degradation that can occur in the first part of the digestive tract, in particular in the rumen, and can instead be released and absorbed in the intestine. Further, the substance or substances carried by the micro particles are protected against the degradation that can occur during pelleting of the animal feed.

DESCRIPTION OF THE INVENTION

The methods and compositions of the present invention relate to a system for the controlled release and protection during pelleting of one or more physiologically or pharmacologically active substances, in the form of micro particles having a size between 0.1 and 5000 microns and intended for use in the zootechnical field and/or the veterinary field. The compositions contain a core which comprises one or more substances having a pharmacological action or playing a role as a feed supplement (hereinafter referred to as active ingredient) and one or more carboxylic acids and/or their salts and eventually one or more excipients. Said core is coated by an outer layer of fats or waxes or a combination of fats and waxes, and preferably by a mixture of glycerides of fatty acids.

Said active ingredient or ingredients are characterized by the presence of an amine functional group within their chemical structure, or more generally contain a functional group with basic characteristics; the core contains also one or more carboxylic acids and/or their salts, characterized by the presence of an acidic functional group within their chemical structure, intimately mixed in the core itself or added on its surface. These carboxylic acids or salts are characterized by the presence of at least one carboxyl group and a lipophilic functional group: the acidic function interacts with the basic function of the active ingredient and the lipophilic functional group helps to increase the lipophilicity of the core favoring the adhesion of the outer fat layer with the core itself.

Examples of active ingredients with a basic functional group suitable for the purpose cited above include, but are not limited to: isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, choline, betaine, carnitine, thiamine, pyridoxine, streptomycin, colistin, tiamulin, neomycin, arginine, glucosamine, niacinamide and their salts, particularly choline chloride, betaine hydrochloride, lysine hydrochloride, thiamine hydrochloride, thiamine mononitrate, pyridoxine hydrochloride, colistin sulfate, and tiamulin fumarate. Examples of carboxylic acid with an acidic functional group suitable for the purpose cited above include but are not limited to: medium to long chain saturated and unsaturated fatty acids and their salts like lauric, palmitic, stearic, oleic arachidic acids and their salts, aromatic carboxylic acids like benzoic acid and its salts, dicarboxylic acids like adipic, sebacic acids and their salts.

It is optionally possible to add excipients to the core of the microparticles according to the present invention. These excipients are capable of improving the formation of the core and can also contain a basic function in their chemical structure. Examples of excipients suitable for the purpose cited above include but are not limited to, are: clay, cob meal, silica, silicates, microcrystalline cellulose, polyvinylpyrrolidone, calcium phosphate, starch, alginate, amino modified silica, amino modified clays, amino modified cellulose, acrylic polymers with amine groups, chitosan, and gelatin. These excipients are typically used in an amount comprised between 0 and 40% of the total weight of the core.

Said core is coated by an outer layer of fats or waxes, and preferably by a mixture of glyceride of fatty acids. The ability to control release effectively is determined by the synergistic action of two phenomena: an interaction between the basic function and the carboxyl group in the core, and the barrier effect of the outer fat layer.

The controlled-release and protection against degradation during pelleting system according to the present invention is provided by preparing micro particles with a method which is composed of the steps as described below.

A mixture is prepared which comprises the active ingredient or ingredients and the carboxylic acid or acids. The amount of active or actives is comprised between 30 and 100% and preferably between 50 and 100%, even more preferably between 60 and 100% of the weight of the mixture. The amount of the carboxylic acid or acids is comprised between 0 and 70%, and preferably between 0 and 50%, even more preferably between 0 and 40%. Mixing can be performed with conventional fixed- or rotating-body mixers, since the choice of the type of mixer is not particularly critical with respect to the intended result. Starting from said mixture, microgranules are formed with the techniques commonly described for processes for granulation or agglomeration in the pharmaceutical field and in the food or feed industry. Examples in this regard are described abundantly in specialist literature, such as for example in Pharmaceutical principles of solid dosage forms, J. T. Carstensen (Ed.) (1993), Technomic Publishing Co., Lancaster (USA), or Pharmaceutical Pellettization Technology I. Ghebre-Sellassie (Ed.) (1989), Marcel Dekker, New York (USA), or Principi di tecnologie farmaceutiche, P. Colombo et al.

(Eds.) (2004), Casa Editrice Ambrosiana, Milan (Italy), and are represented for example by the processes of extrusion-spheronization, fluid-bed granulation, rotating plate granulation, high-speed granulation, wet granulation, melt granulation, melt extrusion, melt agglomeration.

As an alternative to the method described above, the powder of the core can be transformed into micro granules by spraying it or mixing it with an aqueous solution which contains the active ingredient or ingredients. In this case, the concentration of said solution is comprised between 0.05 and 0.95 g/ml and preferably between 0.2 and 0.8 g/ml. The amount of solution of active substance that is added is such that the amount of active ingredient is comprised between 0.1 and 50% by weight of the core and preferably between 0.5 and 40% by weight of the core, even more preferably between 1 and 30% by weight of the core.

In this case also, the method for producing the granules can be for example extrusion-spheronization, fluid-bed granulation, rotating plate granulation, high-speed granulation, wet granulation, melt granulation, melt extrusion and melt agglomeration.

As an alternative to the method described above, the carboxylic acid or acids can be added to the core by spraying it or them on the surface of the preformed microgranules. In this case also the amount of carboxylic acid or acids is comprised between 0 and 70%, and preferably between 0 and 50%, even more preferably between 0 and 40% by weight of the core. Said acid or acids can be applied to the surface of the cores prepared as described earlier, after melting said acid or acids, by means of a so-called fluid bed or spray congealing technique or by drum mixer coating or in any case with a coating method such as those shown for example in the monograph Coated pharmaceutical dosage forms. Fundamentals, manufacturing techniques, test methods and raw materials, K. H. Bauer, K. Lehmann, H. P. Hosterwald, G. Rothgang (Edts), CRC Press, Boca Raton 1998.

It is optionally possible to add to the core, excipients which are capable of improving the formation of micro granules, in an amount comprised between 0 and 40% of the weight of the core and preferably between 0 and 30%. These excipients can be added to the core as powder or solubilized into aqueous solution.

In case the active ingredient is available in its pure (>96%) form as a granulate there may be no excipient needed to e.g. absorb a liquid product. In that case the preferred concentration of the excipients used for the production of the core is between 0 and 20%

In all the production methods described above, once the granules or microgranules have been obtained, they are dried if necessary with a drying method which uses a static or dynamic bed.

The cores thus obtained are coated with a layer of fats or waxes, and preferably by a mixture of glycerides of fatty acids with a melting point comprised between 50 and 80° C. and preferably between 55 and 62° C. The fat is constituted preferably of mixtures of hydrogenated fatty acid glycerides. In particular, the preferred conditions provide for a C-16 fatty acid triglyceride content comprised between 40 and 70% and C-18 between 30 and 50% of the total fatty acid content. Those skilled in the art will appreciate the need for adequate temperature control to maintain the active and fat or wax matrix in a consistent state during manufacture depending on the method of coating being used. As the viscosity of the matrix can rise rapidly with increases in moisture content of the core, resulting in problems forming a consistent product, the storage conditions of the actives and cores should be carefully controlled, particularly if the active or core is hygroscopic, such as is the case with lysine.

Said fat can be applied to the surface of the cores prepared as described earlier, after melting said fat, by means of a so-called fluid bed or spray congealing technique or by drum mixer coating or in any case with a coating method such as those shown for example in the monograph Coated pharmaceutical dosage forms. Fundamentals, manufacturing techniques, biopharmaceutical aspects, test methods and raw materials, K. H. Bauer, K. Lehmann, H. P. Hosterwald, G. Rothgang (Edts), CRC Press, Boca Raton 1998.

The total amount of said coating fat applied is between 10 and 60% and preferably between 15 and 50% of the final weight of the micro particles.

It is optionally possible to add to the coating fat, excipients which are capable of improving their physical properties such as water resistance, viscosity, plasticity, adhesiveness, stress and temperature stability.

Examples of excipients capable of improving the physical properties of fat include but are not limited to lecithin, clay, silica, terpenes, sterols, calcium and sodium salts.

A particular characteristic of the present invention is that the ability to control the release effectively, and consequently reduce the rumen degradation, of active substances is determined by the synergistic action of two phenomena: an interaction between the basic function of the active and the acidic function of the carboxylic acid contained in the core; and the barrier effect of the coating fat layer. The interaction between the basic and acidic functions helps to slowing down the release of the active. This ability to control the release is verified with a 24 hours water dissolution test performed with an USP paddle apparatus (Apparatus 2) at 100 rpm and 38° C., the release after a 24-hours dissolution test is less than 30% of the content of the actives.

By way of non-limiting demonstration, examples related to the preparations and characteristics of the invention are cited hereafter.

EXAMPLE 1. Controlled-Release Formulation Based on a Core that Contains Active Ingredients and Carboxylic Acid Intimately Mixed in it

TABLE 1

| | | Composition: | |
|---|---|---|---|
| Core | Active ingredient | L-Lysine monohydrochloride (ADM, Decatur Illinois, USA) | 12.6 kg |
| | | L-Lysine in aqueous solution at 50% (ADM, Decatur Illinois, USA) | 2 kg |
| | Carboxylic acid | Stearic acid (BBC srl, Torre Boldone BG, IT) | 2 kg |
| Coating layer | Fat | Vegetoil S, hydrogenated vegetable oil (BBC srl, Torre Boldone BG, IT) | 4.4 kg |

The dry L-lysine monohydrochloride was mixed with liquid basic L-Lysine and stearic acid at 70° C. in a ploughshare mixer for 30 minutes. The core was then cooled to 40° C. and the coating layer was applied at 65° C. by spraying it in a pan coater. The microparticles were then cooled to under 45° C.

A release dissolution test was performed with a USP paddle apparatus (Apparatus 2) at 38° C. and 100 r.p.m, in 700 ml of distilled water.

After 24 hours the released L-lysine was 18.7% with a standard deviation of 0.8.

EXAMPLE 2. Controlled-Release Formulation Based on a Core that Contains Active Ingredients and Carboxylic Acid Added on their Surface

TABLE 2

| | | Composition: | |
|---|---|---|---|
| Core | Active ingredients | L-Lysine monohydrochloride (ADM, Decatur Illinois, USA) | 240.38 kg |
| | | L-Lysine in aqueous solution at 50% (ADM, Decatur Illinois, USA) | 9.62 kg |
| | Carboxylic acid | Stearic acid (BBC srl, Torre Boldone BG, IT) | 44.6 kg |
| Coating layer | | Vegetoil S, hydrogenated vegetable oil (BBC srl, Torre Boldone BG, IT) | 62.4 kg |

The dry L-lysine monohydrochloride was mixed with liquid basic L-Lysine at 45° C. in a ribbon blender. The liquid was sprayed on the dry L-lysine monohydrochloride using a spraying nozzle at 2 barr pressure over a time of 5 minutes. The granules were then dried in a fluid bed. Stearic acid at 70° C. was added to the surface of the preformed microgranules by spraying it in a pan coater. The core was then cooled to 40° C. and the coating layer was applied at 65° C. by spraying it in a pan coater. The microparticles were then cooled to under 45° C.

A release dissolution test was performed with a USP paddle apparatus (Apparatus 2) at 38° C. and 100 r.p.m, in 700 ml of distilled water.

After 24 hours the released L-lysine was 6.0% with a standard deviation of 0.6.

EXAMPLE 3. Use of an Excipient in the Coating Layer

TABLE 3

| | | Composition: | |
|---|---|---|---|
| Core | Active ingredients | L-Lysine monohydrochloride (ADM, Decatur IL, USA) | 6523.8 g |
| | | L-Lysine in aqueous solution at 50% (ADM, Decatur IL, USA) | 476.2 g |
| | Carboxylic acid | Stearic acid (BBC srl, Torre Boldone BG, IT) | 1000 g |
| coating layer | fat | Vegetoil S, hydrogenated vegetable oil (BBC srl, Torre Boldone BG, IT) | 1980 g |
| | excipient | Soy lecithin | 20 g |

The dry L-lysine monohydrochloride was mixed with liquid L-lysine at 45° C. in a rotary granulating machine. The granules were then dried in a fluid bed. Stearic acid at 70° C. was added to the preformed microgranules by spraying it in a pan coater. The core was then cooled at 40° C. and coated at 65° C. with the liquid fat containing the lecithin. The microparticles were then cooled to under 45° C.

A release dissolution test was performed with a USP paddle apparatus (Apparatus 2) at 38° C. and 100 r.p.m, in 700 ml of distilled water.

After 24 hours the released L-lysine was 13.8% with a standard deviation of 0.4.

COMPARATIVE EXAMPLE 4. Formulation without the Carboxylic Acid in the Core

In order to demonstrate the importance of the interaction between the basic function of the active with the carboxylic acid a formulation without the carboxylic acid and with the coating fat layer only was also produced and tested for release of the active ingredient.

TABLE 4

| | | Composition: | |
|---|---|---|---|
| Core | Active ingredients | L-Lysine monohydrochloride (ADM, Decatur Illinois, USA) | 7810 g |
| Coating layer | fat | Vegetoil PH, hydrogenated vegetable oil (BBC srl, Torre Boldone BG, IT) | 3190 g |

The dry L-lysine monohydrochloride was coated with liquid hydrogenated vegetable oil 70° C. This was accomplished in a pan coater. The micro particles were than cooled to under 45° C.

A release dissolution test was performed with an USP paddle apparatus at 38° C. and 100 r.p.m, in 700 ml of distilled water.

After 24 hours the released L-lysine was 80%.

EXAMPLE 5. Controlled-Release Formulation Based on a Core that Contains Active Ingredient and Carboxylic Acid Salt Intimately Mixed in it

TABLE 5

| | | Composition: | |
|---|---|---|---|
| Core | Active ingredient and carboxylic acids salt | Taminizer ® C (Taminco N.V., Gent, Belgium) | 210 kg |
| Coating layer | fat | Vegetoil S, hydrogenated vegetable oil (BBC srl, Torre Boldone BG, IT) | 199 kg |
| | excipient | Soy lecithin | 1 kg |

Taminizer® C is a commercial brand product made according to patent application WO2010072842 A1 and containing choline chloride and at least one salt of medium to long chain fatty acid. Taminizer® C was used as a core and it was coated at 65° C. with the liquid fat, containing the lecithin, by spraying it in a pan coater. The microparticles were then cooled to under 4 5° C.

A release dissolution test was performed with a USP paddle apparatus (Apparatus 2) at 38° C. and 100 r.p.m, in 700 ml of distilled water.

After 24 hours the released choline chloride was 12.9% with a standard deviation of 0.6.

EXAMPLE 6. Controlled-Release Formulation Based on a Core that Contains an Excipient at Very Low Concentration

TABLE 6

| | | Composition: | |
|---|---|---|---|
| Core | Active ingredient | DL-methionine (Sumitomo Chemical, Tokyo, Japan) | 9730 g |
| | excipient | Starch licatab M (Roquette, Freres 62136 Lestrem France) | 270 g |
| | water | FU distilled water ACEF spa (Fiorenzuola, PC, IT) | 675 ml |
| | Carboxylic acid | Stearic acid (BBC srl, Torre Boldone BG, IT) | 1785 g |
| coating layer | fat | Vegetoil S, hydrogenated vegetable oil (BBC srl, Torre Boldone BG, IT) | 2500 g |

The dry DL-methionine was mixed with starch and water in the chamber of a rotary granulating machine. The granules were then dried in a fluid bed. Afterwards the stearic acid at 70° C. was added to the preformed microgranules by spraying it in a pan coater. The core was then cooled to 40° C. and the coating layer was applied at 65° C. The microparticles were then cooled to under 45° C.

A release dissolution test was performed with an USP paddle apparatus (Apparatus 2) at 38° C. and 100 r.p.m, in 700 ml of distilled water.

After 24 hours the released DL-methionine was 11.4% with a standard deviation of 1.2.

EXAMPLE 7. Controlled-Release Formulation Based on a Core that Contains an Excipient at High Concentration

TABLE 7

| | | Composition: | |
|---|---|---|---|
| Core | Active ingredient and excipient | Choline Chloride 70% on cereal carrier (Balchem Corporation, NY, USA) | 4000 g |
| | | L-lysine in aqueous solution at 50% (ADM, Decatur Illinois, USA) | 143 |
| | carboxylic acid | Stearic acid (BBC srl, Torre Boldone BG, IT) | 857 g |
| coating layer | fat | Vegetoil S, hydrogenated vegetable oil (BBC srl, Torre Boldone BG, IT) | 3489.5 g |
| | excipient | Soy lechitin | 10.5 g |

Choline Chloride 70% is a dry commercial product containing choline chloride on a cereal carrier. It was mixed with liquid basic L-Lysine and stearic acid at 70° C. in a ploughshare mixer for 30 minutes. The core was then cooled to 40° C. and the coating layer was applied at 65° C. by spraying it in a pan coater. The microparticles were then cooled to under 45° C.

A release dissolution test was performed with an USP paddle apparatus (Apparatus 2) at 38° C. and 100 r.p.m, in 700 ml of distilled water.

After 24 hours the released choline chloride was 4.0% with a standard deviation of 2.1.

EXAMPLE 8. Protection Against Degradation During Pelleting

The micro particles were prepared as in Example 3 and are referred to in this example as USA Lysine™. The study is a replicated 4×4 Latin Square design using eight steers (276±24 kg) that were fed a TMR twice daily, (14.9% CP, 2.75 Mcal/kg ME) ad libitum with 60% of the TMR offered at 8:00 a.m. and the remainder 12 h later. On the $7^{th}$ day, plasma was collected through jugular veinipuncture at 0, 2, 4, 6 and 8 h post-feeding. Each plasma sample was analyzed for L-lysine content, [p-Lys]. Dietary Lys treatments were offered as USA Lysine™ and supplied as 3 types of incorporations into the grain mix: hand mixed (50 and 100 g; HSO and H100), mechanical mixed (100 g; M100) and as pellets (100 g; P100). The results of HSO did not increase [p-Lys] over the basal diet. The [p-Lys] concentrations of H100, M100 and P100 were different from the basal diet (P<0.0001). Mechanical mixing and pelleting of USA Lysine™ in the top-dress did not affect [p-Lys] compared with hand mixed. Regardless of dietary incorporation method, the regression equation applied to the [p-Lys] of steers fed 100 g of USA Lysine™, predicts at least 50% bioavailability of Lys from USA Lysine™. Specifically, 53.88% was bioavailable from the H100 incorporation, 54.76% from the M100 incorporation and 51.31% from the P100 incorporation. That the bioavailability of the active ingredient did not significantly diminish even though the micro particles had been processed into a pelleted feed was surprising.

EXAMPLE 9. Protection Against Degradation During Pelleting

Materials and Methods

A commercially available protected form of lysine, LysiPEARL™ (Kemin Industries, Inc., Des Moines, Iowa) was added to a concentrate feed and pelleted according to industry recommendations. Two physical forms of feed were used: (1) concentrate feed, meal form, as a control; and (2) concentrate feed, pellet form. The product was added to the meal form of the concentrate feed comprised of dehulled soybean meal, corn gluten meal, corn distillers dried grains and extruded soybeans, having 85.5% dry matter, 38.0% crude protein, 5.0% crude fat and 6.0% crude fiber. The mixture was pelleted using a standard pellet mill for ruminant feed. Based on the typical diet inclusion percentage for LysiPEARL™ and the feeding percentage for a complete grain mix, the concentration of LysiPEARL™ in the feed was approximately 0.35% on an as-fed basis (AF). A slightly greater concentration could be justified by arguing that LysiPEARL™ could be included in a lower inclusion product base such as a protein mix rather than a complete grain mix. This product base would then increase the practical concentration to a value close to 1.00% AF.

The background concentration of lysine was expected to be 2.61% in the basis feed (not supplemented) and 2.78% in those treatments supplemented with 0.35% (AF) LysiPEARL™. It is estimated that the amount of lysine that would be present after ruminal incubation would be approximately 50% of the values stated above. Thus, if 16 g of the treatment were incubated (8 replications multiplied by 2 g for each replication), then there would be 220 mg of lysine after 16 hours of ruminal incubation.

The experimental design produced 5 treatments (Table 8).

TABLE 8

| Treatments | |
|---|---|
| Treatment ID | Description |
| 1 | Concentrate, meal form |
| 2 | Concentrate, pellet form |

TABLE 8-continued

| | Treatments |
|---|---|
| Treatment ID | Description |
| 3 | Concentrate, meal form with LysiPEARL |
| 4 | Concentrate, pellet form with LysiPEARL |
| 5 | LysiPEARL product form |

Approximately 2 g of each treatment was placed into each IV bag at 8 replications. The extent of in-vitro (IV) ruminal digestion was measured after 16 hours. The constituents monitored were dry matter and lysine. Approximately 3 L of rumen fluid and 200 g of fiber mat were collected from each of 4 donor Jersey steers at 1 hour post-prandial. The 12 L of ruminal contents were composited and aliquots were mixed with Van Soest buffer so that 600 ml of the buffered ruminal contents were distributed among the IV vessels and volume raised to 1800 ml using distilled water. All procedures were under a stream of carbon dioxide in each IV vessel. After the ruminal contents and buffer were mixed, the IV bags were added to the IV vessels which remained under carbon dioxide. The IV vessels were then placed into an air-jacketed, anaerobic incubator at a pH of 6.5, 38° C. and an environment of 3% carbon dioxide and artificially ruminated each 3 hours.

Post-ruminal or gastric/intestinal IV incubations were conducted in three phases: Phase 1, gastric; Phase 2, illeal; and Phase 3, wash out. The Phase 1 solution consisted of 50% hydrochloric acid in distilled water plus 0.1 g pepsin in 500 ml then raised to 1800 ml. Phase 2 solution consisted of pH 8 phosphate buffer plus a semi-purified enzymatic cocktail consisting of pancreatic amylase (0.75 g), lipase (0.75 g) and pancreatin (0.75 g) then raised to 1800 ml. Phase 3 was soaking in a water solution of sodium azide and sodium lauryl sulfate at 11° C. to remove adhering micro-organisms.

After each IV incubation, the IV bags were dried in a forced-air oven at 20° C. until a constant weight. The dry bags were sent for analysis of lysine. Lysine concentration in the dry contents of the appropriate IV bags (digestive residue) was measured by AOAC 994.12.

Statistics were performed using the appropriate models in XLSTAT (release 2007.5, updated in 2012, Addinsoft USA, NY).

Discussion

The main objective of this study was to quantify the effect of physical form (meal versus pellet) of a concentrate or complete feed on the digestive properties of a commercial protected lysine supplement. Rumen escape of the active molecule is the measurement of the amount of the molecule that is not degraded (rumen undegraded) during ruminal incubation (in this study, 16 hours was the length of ruminal incubation).

Rumen undegraded values for LysiPEARL™ containing rumen-protected lysine are shown in Tables 9 (meal form) and 10 (pellet form) along with intestinal digestibility (amount of digestion (gastric and illeal) of the material that is not ruminally degraded (the digestibility of rumen undegraded lysine). Rumen undegraded material can also be called: rumen bypass material, or rumen escape material.

TABLE 9

Digestive properties of lysine in meal

| Treatment ID | Initial % lysine | Ruminal IV % lysine | Rumen Undegraded | Intestinal IV % lysine | Total tract IV % lysine | Total tract Undegraded |
|---|---|---|---|---|---|---|
| 1 | 1.71 | 24.62 | 75.38 | 73.05 | 73.11 | 26.89 |
| 5* | 37.19 | 71.42 | 26.58 | 92.51 | 92.56 | 7.44 |
| 3 | 2.08 | 35.84 | 64.16 | 72.87 | 72.96 | 27.04 |

*LysiPEARL™

TABLE 10

Digestive properties of lysine in pellets

| Treatment ID | Initial % lysine | Ruminal IV % lysine | Rumen Undegraded | Intestinal IV % lysine | Total tract IV % lysine | Total tract Undegraded |
|---|---|---|---|---|---|---|
| 2 | 1.76 | 18.95 | 81.05 | 67.68 | 66.85 | 33.15 |
| 5* | 37.19 | 71.42 | 28.58 | 93.38 | 93.43 | 6.57 |
| 4 | 2.07 | 33.03 | 66.97 | 72.54 | 72.63 | 27.37 |

*LysiPEARL™

A comparison of the data in Tables 9 and 10 reveals that the amount of lysine available at the intestinal level of the animal, thereby by-passing the rumen (Total tract IV % lysine) is almost the same in the pellet form (72.63) as it is in the meal form (72.96). Accordingly, the lysine in LysiPEARL was sufficiently protected to avoid degradation by the heat and pressures of pelleting.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art that have the disclo-

We claim:

1. A method of feeding a pelleted feed product to ruminants, the method comprising:
providing the ruminants a pelleted feed product, the pelleted feed product comprising a micro particle and at least one additional feed component, the micro particle comprising a mixture of at least one active substance and at least one carboxylic acid and/or salt thereof, wherein the mixture is embedded within a fatty substance, further wherein:
the at least one active substance is selected from a group consisting of isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, betaine, carnitine, thiamine, pyridoxine, streptomycin, colistin, tiamulin, neomycin, arginine, glucosamine, niacinamide and their salts, betaine hydrochloride, lysine hydrochloride, thiamine hydrochloride, thiamine mononitrate, pyridoxine hydrochloride, colistin sulfate, and tiamulin fumarate,
the at least one carboxylic acid and/or salt thereof is characterized by the presence of an acidic functional group and at least one lipophilic functional group,
the fatty substance comprises one or more of a composition selected from a group consisting of waxes, fats, vegetable oil, and glycerides of fatty acids, and
the at least one additional feed component is selected from a group consisting of dehulled soybean meal, corn gluten meal, corn distillers, dried grains, and extruded soybeans,
wherein the at least one active substance includes a basic functional group that interacts with the acidic functional group of the carboxylic acid and/or salt thereof, and the lipophilic functional group adheres to the fatty substance such that the fatty substance defines an outer fat layer that protects the at least one active substance from the at least one additional feed component in the pelleted feed product,
wherein, in response to ingesting the pelleted feed product, the protected at least one active substance remains protected from ruminal degradation and available for absorption in an intestine, and
wherein the micro particle has a size between 0.1 and 5000 microns.

2. The method as defined in claim 1, wherein the at least one active substance is present in an amount between 50 and 100% by weight of the mixture.

3. The method as defined in claim 1, wherein the at least one active substance is present in an amount between 60 and 100% by weight of the mixture.

4. The method as defined in claim 1, wherein the at least one carboxylic acid and/or salt thereof is present in an amount between 0.1 and 50% by weight of the mixture.

5. The method as defined in claim 1, wherein the at least one carboxylic acid and/or salt thereof is present in an amount between 0.1 and 40% by weight of the mixture.

6. The method as defined in claim 1, wherein the fatty substance has a melting point of between 55° C. and 62° C.

7. The method as defined in claim 1, wherein the amount of fatty substance is between 15 and 50% of the final weight of the active substance, the at least one carboxylic acid and/or salt thereof, and the fatty substance.

8. The method as defined in claim 1, wherein the at least one active substance content is between about 0.35% and about 1% by final weight of the pelleted feed product on an as-fed basis.

9. The method as defined in claim 1, wherein the at least one carboxylic acid and/or salt thereof is selected from the group consisting of short, medium and long chain saturated and unsaturated fatty acids and their salts consisting of butyric, myristic, lauric, palmitic, stearic, oleic and arachidic acids and their salts, benzoic acid and its salts, and dicarboxylic acids consisting of adipic and sebacic acids and their salts.

10. The method as defined in claim 1, wherein the mixture further comprises excipients.

11. The method as defined in claim 10, wherein the excipients comprise a basic functional group.

12. The method as defined in claim 10, wherein the excipients are selected from the group consisting of clay, cob meal, silica, silicates, microcrystalline cellulose, polyvinylpyrrolidone, calcium phosphate, calcium carbonate, magnesium oxide, starch, alginate, amino modified starches, amino modified silica, amino modified clays, amino modified cellulose, acrylic polymers with amine groups, chitosan, and gelatin.

13. The method as defined in claim 10, wherein said excipients are present in an amount between 0.1 and 40% by weight of the mixture.

14. The method as defined in claim 1, wherein the at least one active substance is present in an amount between 30 and 100% by weight of the mixture.

15. The method as defined in claim 1, wherein the at least one carboxylic acid and/or salt thereof is present in an amount between 0.1 and 70% by weight of the mixture.

16. The method as defined in claim 1, wherein the fatty substance has a melting point of between 50° C. and 80° C.

17. The method as defined in claim 1, wherein the glycerides are mixtures of hydrogenated fatty acid glycerides.

18. The method as defined in claim 17, wherein said hydrogenated fatty acid glycerides comprise a C-16 fatty acid triglyceride content of between 40 and 70 weight % and a C-18 fatty acid triglyceride content of between 30 and 50 weight % of a total fatty acids content.

19. The method as defined in claim 1, wherein the amount of the fatty substance is between 10 and 60% of the final weight of the active substance, the at least one carboxylic acid and/or salt thereof, and the fatty substance.

* * * * *

UNITED STATES PATENT AND TRADEMARK OFFICE
CERTIFICATE OF CORRECTION

Page 1 of 1

PATENT NO. : 9,986,749 B2
APPLICATION NO. : 13/957877
DATED : June 5, 2018
INVENTOR(S) : Boucher et al.

It is certified that error appears in the above-identified patent and that said Letters Patent is hereby corrected as shown below:

In the Specification

| Column | Line | PTO | Should Be |
|---|---|---|---|
| 2 | 7 | "not limitated to:" | -- not limited to: -- |
| 7 | 43 | "143" | -- 143 g -- |
| 8 | 10 | "HSO" | -- H50 -- |
| 8 | 11 | "HSO" | -- H50 -- |

Signed and Sealed this
Ninth Day of October, 2018

Andrei Iancu
*Director of the United States Patent and Trademark Office*